United States Patent
Stoodley

(10) Patent No.: US 6,611,846 B1
(45) Date of Patent: Aug. 26, 2003

(54) METHOD AND SYSTEM FOR MEDICAL PATIENT DATA ANALYSIS

(75) Inventor: Marcus A. Stoodley, Sydney (AU)

(73) Assignee: Medtamic Holdings, St. Leonards (AU)

(*) Notice: Subject to any disclaimer, the term of this patent is extended or adjusted under 35 U.S.C. 154(b) by 0 days.

(21) Appl. No.: 09/430,782

(22) Filed: Oct. 30, 1999

(51) Int. Cl.⁷ .............................................. G06F 17/30
(52) U.S. Cl. ........................................ 707/104.1; 705/3
(58) Field of Search ............................ 707/104.1; 705/3

(56) References Cited

U.S. PATENT DOCUMENTS

| | | | | |
|---|---|---|---|---|
| 5,296,688 A | * | 3/1994 | Hamilton et al. ............ 235/375 |
| 5,740,801 A | * | 4/1998 | Branson ...................... 600/407 |
| 5,805,118 A | * | 9/1998 | Mishra et al. ................ 345/1.1 |
| 5,903,889 A | * | 5/1999 | de la Huerga et al. ......... 707/10 |
| 5,920,317 A | * | 7/1999 | McDonald ................... 345/835 |
| 6,047,259 A | * | 4/2000 | Campbell et al. .............. 705/3 |
| 6,108,635 A | * | 8/2000 | Herren et al. ................ 600/300 |
| 6,177,940 B1 | * | 1/2001 | Bond et al. .................. 434/262 |
| 6,208,974 B1 | * | 3/2001 | Campbell et al. .............. 705/3 |
| 6,234,964 B1 | * | 5/2001 | Iliff ............................ 600/300 |
| 6,246,975 B1 | * | 6/2001 | Rivonelli et al. ........... 128/920 |
| 6,272,481 B1 | * | 8/2001 | Lawrence et al. ............ 706/10 |
| 6,282,531 B1 | * | 8/2001 | Haughton et al. ............ 706/46 |
| 6,353,817 B1 | * | 3/2002 | Jacobs et al. ................ 706/50 |
| 6,438,533 B1 | * | 8/2002 | Spackman et al. ........... 706/45 |

* cited by examiner

*Primary Examiner*—Wayne Amsbury
(74) *Attorney, Agent, or Firm*—Lisa N. Benado

(57) ABSTRACT

The storage and retrieval of medical information is provided by use of a database that facilitates accurate clinical audit, research and/or presentation activities. Comprehensive patient information may be retrieved based on patient descriptive categories including the anatomy, pathology or clinical presentation, treatment and outcome factors of each case. The categories include data options that may be organized in the form of a hierarchical tree that has branching levels of data options with decreasing specificity. Data from the various levels may be compared, as well as data between individual categories. In some embodiments, selected multimedia data may be accessed based on criteria from data options of the patient descriptive categories.

40 Claims, 12 Drawing Sheets

OPERATION TABLE — 150

| Patient ID | Date | Operation | Duration | Surgeon | Asst.1 | Asst. 2 | Anesthes. | Related Diagnoses | Operation ID |
|---|---|---|---|---|---|---|---|---|---|
| A | 1/11/98 | Op 1 | 6:45 | Weir | Stoodley | Masnyk | | RD1 | 1 |
| B | 1/11/98 | Op 2 | 0:30 | Smith | | | | | 2 |

FIG. 4A

OPERATION CODES TABLE — 160

| Operation ID | Code |
|---|---|
| 1 | Clip Aneurysm |
| 1 | Temporal Clip |
| 1 | Hair Cut |
| 2 | Wrap/Gauze |

FIG. 4B

ANATOMY DATA OPTION TABLE

| Level 1 | Level 2 | Level 3 | Level 4 | Level 5 |
|---------|---------|---------|---------|---------|
| Upper Limb | Elbow | | | |
| Upper Limb | Hand | | | |
| Upper Limb | Hand | Index Finger | | |
| Upper Limb | Hand | Thumb | | |

METHOD AND SYSTEM FOR MEDICAL PATIENT DATA ANALYSIS

FIELD OF THE INVENTION

The present invention relates generally to the storage and retrieval of medical information using a computer, and more particularly to a method of analyzing a comprehensive collection of medical patient data through the use of a medical database.

BACKGROUND

In many fields of medicine, e.g. neurology, cardiology, surgery, etc., it is often useful to retain patient data in a manner that is readily available for future evaluation. Storage and manipulation of medical data are especially desirable in accessing the facts for analysis, where medical practitioners perform clinical research and quality assurance of medical care.

Traditionally, patient information is stored on hard copy files and in large electronic storage archives, e.g. hospital information systems (HIS). Such storage mediums usually only contain data from a local healthcare site and not data from remote locations. These storage means are generally adequate for retrieval of information about individual patients.

However, it is also very useful to view multiple patient data in aggregate and to compare the data, such as with the assistance of a computer database. The access and review of medical data from cases having similarities to a current case may assist in the treatment of a patient. In other applications, transformation of raw clinical data into comprehensive information provides invaluable knowledge. Computer databases may assist in storing a cohort description of data to describe a group of patients that have a common attribute. Furthermore, data patterns may be analyzed in terms of trends or associations with the use of databases. By predictive modeling, data may be used to derive knowledge of relationships and provide quality assurance of a medical entity.

Quality assurance of medical treatment includes the assessment of many factors. The level of care furnished by medical providers may be determined by the degree to which health services increase the likelihood of a desired health outcome. In general, level of care involves assessment of risk factors compared to outcome. The structure of care may also be evaluated by reference to the facility, the equipment, the services, the personnel available for care, and the qualifications of the involved health professionals. The process of care is another factor that includes the services provided and the process by which patients are moved through the system. Accessibility may be determined by the degree of ease or difficulty that individuals have in obtaining healthcare. Furthermore, appropriateness of care is the extent to which care complies with accepted or is within standard practice of the community, including costs and charges. Is there supposed to be a journal name here? 1995;60:1514–21.

The type of information that is availability for use in analysis is critical for conducting fair assessments of care. Databases should include precise definitions of all the terms used in order to avoid inaccurate reporting. Comparisons across patients and healthcare institutions require adequate description of those patients studied in order to group those having comparable probabilities in response to other treatment, i.e. must discriminate between groups of patients. The data should also be useful in plotting the course of illness. Rules for ranking data should be objective, reproducible, meaningful and reliable.

Furthermore, a comprehensive selection of data that is appropriate for quality assurance and research must be stored. Excluded information may result in skewed conclusions. For example, where an audit is performed on outcomes of one treatment regimen, e.g. surgery, descriptions of clinical presentations and other treatments should be considered. Otherwise, medical practitioners who refuse particular treatments for advanced cases produce more favorable outcome data for the remaining treated patients. If no treatment is performed, this information should be recorded and taken into consideration in the assessment of outcomes and quality assurance. In addition, if some risk factors are excluded from the data, a higher observed-to-expected ratio results. Gaming may also occur, where risk factors are over reported by a healthcare facility. Well planned databases allow for cohort studies for determining factors associated with good or bad outcomes.

Currently, databases store limited patient information, often in the form of codes that follow the International Classification of Diseases (ICD-10). In general, the ICD-10 standard indicates the pathology of medical conditions. However, ICD-10 codes are insufficient to accurately conduct most patient data analyses.

The selection of ICD-10 codes to represent the diagnosis of a patient's condition may be biased by various factors, such as the specialty of an admitting physician. For example, in coding for cerebrovascular disease, where the admitting physician is a surgeon, the discharge coding may reflect the condition of specific arteries, whereas if the physician is a neurologist or internist, the code assignment may be more likely to reflect the symptomatic status of the patient. See Inaccuracy of the International Classification of Diseases in Identifying the Diagnosis of Ischemic Cerebrovascular Disease, Neurology, 1997, Sep. 49:3, 660–4. Moreover, for some conditions, the coding system does not have sufficient data options to accurately reflect the condition. See Limits of ICD-9-CM Code Usefulness in Epidemiological Studies of Contact and Other Types of Dermatitis, Am J Contact Dermat., 1998, Sep. 9:3, 176–8. As a result, frequently such codes have proven to be inaccurate representations of patients' conditions.

Furthermore, ICD-10 codes depict only a small portion of the medical information that is useful for specific analytical applications. The ICD-10 codes do not allow for cross comparison between branches of data options and only has limited descriptive information. In order to extract information for research and quality assurance, more coded information is needed, such as clinical symptoms and signs, pathology, anatomy, treatment, outcome and data options thereof.

Moreover, it is advantageous for data storage and manipulation mediums to be flexible, so as to accommodate a variety of information/data. Medical information may take numerous forms, including text, images and video, or variations thereof, such as image overlay data, measurements, coordinates, etc. Information may also be in the form of time-dependent data including sound, such as audio dictation, and waveform data. The data may also be static representations of time-dependent forms, such as curves.

According to most current practices, multimedia data are generally archived by healthcare facilities by a patient identification number. Hence, there is no mechanism to readily access multimedia data that relate to particular patient descriptions, such as treatment, anatomy, pathology, etc. Instead, a patient list must be generated and each individual patient's multimedia records retrieved for review. This process is tedious and inefficient for analyses across large numbers of patients and complex investigations.

Thus, in light of the shortcomings of the various currently available systems, there is still a need for systems that enable simple access to many types of data and from several healthcare sites. In particular, there is a desire for a database that allows for storage and manipulation of a highly descriptive body of medical data that is useful for accurate research and quality analysis. The system should allow for searching across multiple layers of variables. It would be further useful for the information to be available in a form for easy dissemination, such as in presentations and reports.

SUMMARY OF THE INVENTION

In one embodiment, a computer assisted method for analyzing medical patient data by storing and accessing relevant data is provided. The type of data that is stored and the relational manner in which they are stored allow for comprehensive searches. The steps in the method may comprise selecting patient data from a list of data options in at least one category. The categories are clinical presentation, pathology, anatomy, treatment and outcome, although additional categories may also exist. Often, the data options of the categories are arranged in a database within table by decreasing levels of specificity in a hierarchical tree. The patient data are stored with a unique identifier to relate all of the patient data within a data set. In another step, the user conducts a search of stored data by selecting at least one criterion for particular patient data from at least one of the categories. The particular patient data are retrieved.

At various times, the patient data are selected from a list of data options within at least two of the categories, such as treatment and outcome, at least three of the categories, at least four of the categories or all five categories. Furthermore, the list of categories may include a provider category. At least one of the criteria may be employed for particular patient data from this provider category. At still other times, at least one of the data options in at least one of the categories is related to custom prospective data provided in a custom screen table that is created by a user and stored within the database. Conveniently, one method allows for selection of patient data by pointing onto a location on a graphic representation of an anatomy.

A variety of types of analyses are possible with the database. In particular applications, the patient data that are extracted from a query search is analyzed by the database and the statistical results are optionally displayed, such as a graph form, e.g. pie chart, bar chart, etc.

In some methods, multimedia data that are related to the particular patient data by the identifier is retrieved. The multimedia data may include video, image, electronic waveform and sound data, and the like, or combinations thereof. In some cases, the multimedia data is retrieved from a storage component in the relational database. In other instances, the multimedia data is stored on a remote server that is communicatively coupled to the relational database, and retrieved therefrom. In any event, some or all of the multimedia data may be selected and conveniently transferred to a presentation applications file.

A medical patient data analysis system for use in employing the above described methods typically includes a processor; an input device in communication with the processor for receiving patient data; and a storage unit in communication with the processor. The storage unit has a relational database for storing data options within data option category tables by decreasing levels of specificity in a hierarchical tree. The data option category tables are selected from the group consisting of clinical presentation, pathology, anatomy, treatment and outcome. The database is further used for storing patient data of a data set having a unique identifier within category tables, the patient data being chosen from the data options in at least one data option category table. The processor has a means for receiving patient data from the input and storing the patient data in the storage unit; a means for receiving instructions from the input for selecting at least one criterion for particular patient data from at least one category table; and a means for retrieving the particular patient data. In one embodiment, a display that is in communication with the processor is provided.

Still other embodiments may provide a computer readable medium having stored therein a plurality of sequences of instructions, which, when executed by a processor, cause the processor to perform certain steps. Among these steps may be included the steps of receiving medical patient data of a data set from an input device. The patient data consists of a selected data option from a hierarchical tree having data options arranged in decreasing levels of specificity. Another step may be determining whether the patient data includes an identifier. If no identifier is present, the processor attaches a unique identifier to the patient data. The process may facilitate the patient data to be stored in a relational database within tables of categories. The categories may include clinical presentation, pathology, anatomy, treatment and outcome. Responsive to instructions received from the input device, the process may retrieve particular patient data that are associated with at least one selected criterion. The patient data may include multimedia data. Of course, other embodiments may provide only the instructions themselves or the instructions as carried in a data signal by a carrier wave.

According to still further embodiments, a server may be provided for use in analysis of medical patient data, according to the present invention. Such a server may include a network interface for acquiring patient data of a patient set from a network. The patient data is chosen from at least one data option from a hierarchical category tree having data options arranged in decreasing levels of specificity. A storage unit is also provided in the server. The storage unit is coupled to receive the patient data from the data interface and to store the patient data within table of categories selected from the group consisting of clinical presentation, pathology, anatomy, treatment and outcome. The patient data of a data set has an attached unique identifier. Further to the server is usually an assembly unit coupled to the network interface and storage unit to gather selected portions of the patient data in response to instructions from a user station. In alternative embodiments of the server, an activation unit is present for determining whether patient data were received by the user station prior to sending instructions for selected portions of patient data.

In a network system, a user station may be provided having an input device for receiving patient data. A processor in the user station has a means for receiving patient data from the input device. The patient data is at least one chosen data option from a category in a tree format as described above. The category is also selected from the group including clinical presentation, pathology, anatomy, treatment and outcome. The process also typically has a means for forming instructions by selecting at least one criterion from at least one of the categories. The user station may also have a browser for sending the instructions and the patient data into a network and receiving selected portions of patient data from the network.

One method of conducting data analysis using a public network includes assembling the patient data into packets. At least one criterion from at least one category is selected and a request is made to a server for selected medical patient data associate with the at least one criterion. The packets having the patient data are sent into the public network for receipt at the server. Thereafter, the selected patient data is received from the server. In one variation of method, the patient data are encrypted prior to sending the packets into the network.

The benefits of the medical patient data analysis system are direct in that a comprehensive assortment of medical data may be stored for easy access and manipulated for accurate research and quality analysis. The categories provide detailed patient descriptions from which data may be retrieved. The invention also provides a convenient way for multimedia data to be retrieved. Moreover, the relationship of the data options to each other in a hierarchical tree allows for further sophisticated searches to be conducted. Thus, clinical research and quality assurance of healthcare providers is greatly facilitated.

Other features and advantages of these and other embodiments are discussed in detail below.

BRIEF DESCRIPTION OF THE DRAWINGS

The present invention is illustrated by way of example, and not limitation, in the figures of the accompanying drawings in which:

FIGS. 2A–2D are examples of display screens for data entry into one relational database in accordance with the methods described below, wherein FIG. 2A shows a diagnosis screen, FIG. 2B shows a treatment screen, FIG. 2C shows an image screen, FIG. 2D shows a test result screen.

FIGS. 4A–4B are tables illustrative of some of the data structures used in embodiments of the relational database, wherein FIG. 4A is an operation table containing data entered in an operation display screen and FIG. 4B is a table of operation codes entered in an operation display screen and linked to the operation table.

FIG. 5 is a table illustrative of one data structure used in embodiments of the relational database to store data options for an anatomy category.

FIGS. 6A–6B are examples of display screens for searching for particular patient data from data stored in one relational database in accordance with the methods described below, wherein FIG. 6A is a "search for" screen and FIG. 6B is a results screen.

DETAILED DESCRIPTION

A medical data analysis system including a database that facilitates accurate clinical audit, research and/or presentation activities with patient data, and methods of its use, is provided. A relational database is employed to store, to manipulate and to retrieve the data. Comprehensive patient information may be retrieved based on patient descriptive categories including the anatomy, pathology or clinical presentation, treatment and outcome factors of each case. The categories include at least two data options that may be organized in the form of a hierarchical tree branching into multiple levels of data to be searched. Data from the various levels may be compared, as well as data between separate categories. In some embodiments, selected multimedia data may be accessed based on criteria from data options of the patient descriptive categories.

Figure 1:
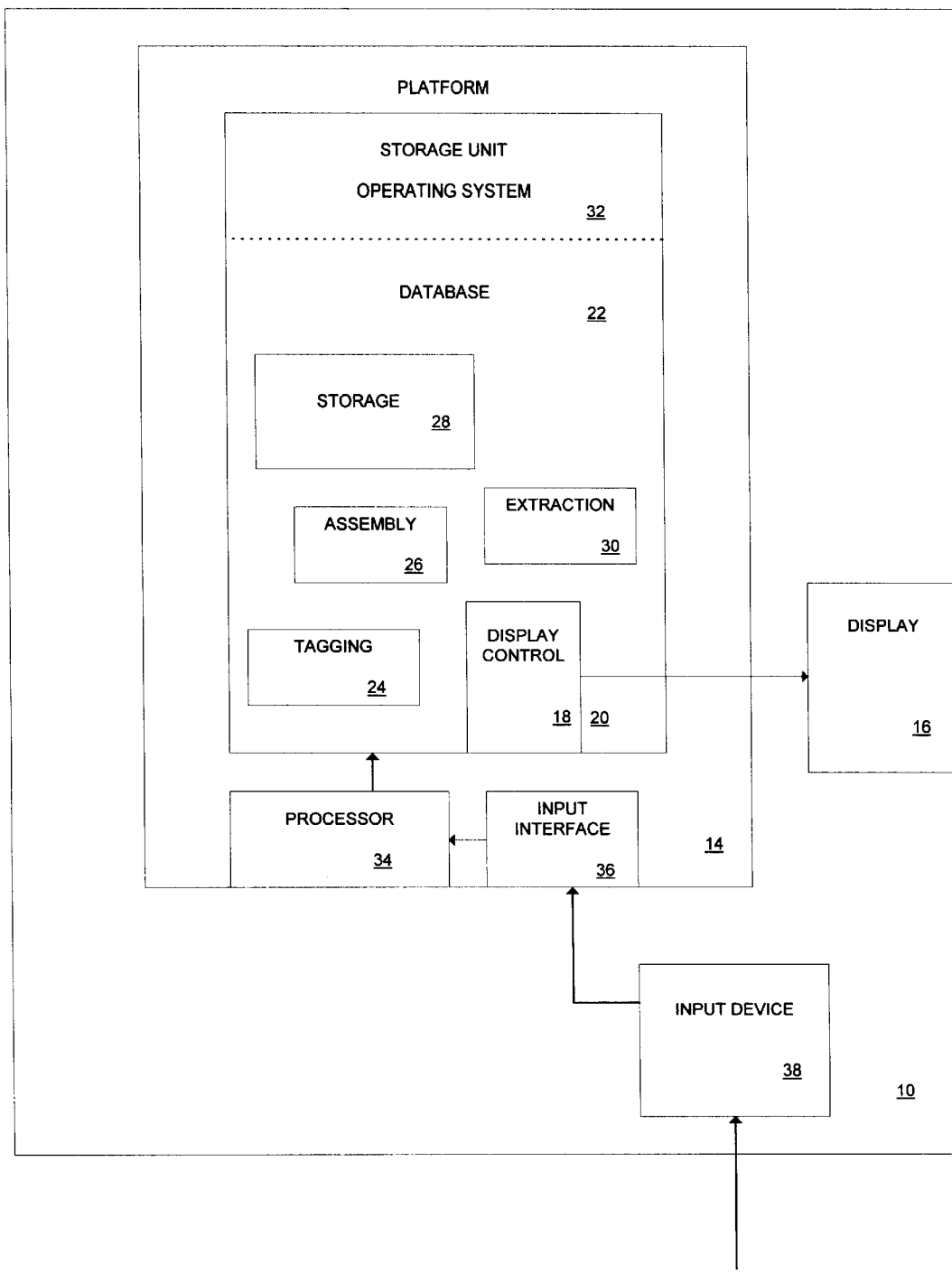
FIG. 1 is a block diagram of one embodiment of the data analysis system comprising a user station, in accordance with the teachings presented herein.

In one configuration of the data analysis system, client-based architecture is used where storage, data processing and computations are performed on a user station. FIG. 1 shows one such data analysis system comprising a user station 10 that is suitable for performing the present method for medical patient data analysis. An input device 12 transmits data from a source to a platform 14. The platform 14 is coupled to a display 16 through a display controller 18. The display may be any one of a number of conventional display devices, such as a liquid crystal display or video display. The platform 14 contains a storage unit 20, a processor 34 and an input interface 36 for communicating to the input device. The storage unit 20 has a database application 22 ("database") for storing, manipulating and retrieving patient data and an operating system 32. The database 22 includes a tagging component 24 for attaching identifiers to the patient data, an assembly component 26 for organizing patient data, a storage component 28, and an extraction component 30 for retrieving particular patient data from storage.

The user station platform 14 may be a personal computer (PC), Macintosh®, or one of a wide variety of hardware platforms that runs the operating system 32. The platform may read and write to and from its storage unit 20. As will be readily apparent to those of ordinary skill in the art, other hardware may be used to execute the software. The operating system may be Windows®, UNIX® or other conventional operating software.

The database 22 may be implemented on a variety of commercially available authoring packages. In some embodiments, the software is written in Visual Basic® with a database tool kit, such as Microsoft Access®, both from Microsoft Corporation, located in Redmond, Wash.

The processor 34 communicates with the database 22 from storage unit 20 to get pieces of code and processes the code. The processor 34 manipulates patient data in accordance with requests from the input device 38 and operates the display controller 40. Processor 34 may have memory, such as random access memory, as is well known in the art.

The storage unit 20 may be any device capable of storing data for a long period of time, either as a component of the platform 14, as shown in FIG. 1, or as a separate entity that is coupled to the platform 14. Although any appropriate storage capacity may be user, the capacity is typically at least ten megabytes and more usually at least twenty gigabytes. Extended storage capabilities are required where multimedia data are stored on the user station. The storage unit may be permanent or removable. For example, the storage unit 20 may be a floppy disk drive, Bernoulli hard drive, Winchester hard disk, analog tape drive, digital tape drive, optical disk drive, magneto-optical drive and floptical disk. In addition, the present invention anticipates other storage devices. All of the aforementioned storage units are by way of example and are not intended to limit the choices that are or may become available in the art.

The input device 38 may be configured to receive data or signals directly from a user. Conventional input devices are keyboards, mouses, microphones, pen-to-text data entry devices, e.g. IBM ThinkPad Untethered Sylus from IBM Corporation, and the like. Other configurations of input devices are data generating modalities. Exemplary medical modalities are data acquisition equipment for magnetic resonance imaging (MRI), computed tomography (CT) ultrasound (US), nuclear medicine (NM), digitized radiography (DR), computer radiography (CR), electronic waveform devices to collect EEG and ECG data, etc. Other modalities include photographic devices, such as high resolution digital cameras, video capture interfaces, such as Snappy® brand parallel port video capture devices, scanners, capture devices for endoscopy and microscopy, etc. In addition, other input devices that transfer data to the platform are within the intended scope of the present invention. In some embodiments of user stations, multiple input devices are present.

It should be noted that the present invention anticipates other components and configurations of the components in the user station of the data analysis system.

Data Storage

In order to store medical patient data, a user prompts the platform to prepare for data entry through the input device. The user may initiate a request for a data storage screen to appear on the display, usually by selecting from a main menu display screen. The user may also specify the medical specialty for which the database is to be used. For example, the user may select a button on the main menu screen that instructs the database that the specialty function is to be neurosurgery, orthopedics, cardiology, or the like. The database will adapt to present to the user the appropriate display screens, menus and data option lists for the select specialty area.

Portions of patient data comprising a data set may be entered at various times and collected from different sources. Each data set is a collection of patient data for an individual patient, recognized in the database by a unique identifier.

Patient data may be grouped under categories of topics and stored as separate and related category tables. The data tables are structured to reach full normalization. Patient demographics are stored in the main table to which other tables are linked by an internally generated identifier that is unique for each patient. In order to achieve normalization, several tables have links to other tables. For example, a first table may link to a second table that contains the descriptive codes for the first table. This structure allows a virtually unlimited number of codes to be entered for each category.

The data may be entered as open text, e.g. into a note field, or chosen from a drop-down list of data options. In addition to text data, the data may be in various graphics and multimedia formats. The data may be in the form of images, overlays, 3-D volumes, electronic waveforms, graphs, curves, videos, sound data, or the like. The medical data may be also be DICOM compliant data (as originally published by an ACR-NEMA committee sponsored by the American College of Radiology and the National Electrical Manufacturers Association as Digital Imaging and Communications in Medicine (DICOM), NEMA Publications PS 3.1-PS3.12, by The National Electrical Manufacturers Association, Rosslyn, Calif., 1992, 1993, 1994, 1995). The display screens may include a combination of text, graphic and multimedia data.

The medical profession is under a strict duty to protect the confidentiality of patients. Thus, protection of medical data/information is of paramount importance. The present data analysis system may include some form of security measures, such as the use of passwords. Password identification determines whether a user is authorized to gain access to the system.

The first data storage screen is usually a default screen, such as a list of stored patient data sets. The user may select a patient from the data set list in order to retrieve the stored data set for that patient. Alternatively, the user may instruct the database that a new data set is to be created for an additional patient.

Data entry display screens may contain a variety of categories for which data may be submitted. Under each category there may be any number of data options, which, when selected by the user, becomes patient data for a data set. Any number of data options may be selected for each category. The data options may be linearly related to each other. The data options may also be hierarchically arranged from general to more specific descriptors under each category. Any number of levels of data options may be available, such as 2 to 10 levels, and usually 3 to 5 levels. On the screen, the branches of data options for each category may be depicted in the form of a hierarchical tree where the levels of data options are graphically shown. In this embodiment, the user may conveniently enter data by pointing to the data option at a particular level and selecting the option.

In other embodiments of data entry screens, the data options are listed in alphabetical order, where the first portion of the option phrase is the descriptor for the first level, followed by the subsequent level descriptors in decreasing order. For example, under the Anatomy category, a data option may be "ICA: at posterior communicating," where the term "ICA" is the first level and the phrase "posterior communicating" is the next lower level. Alternatively, the various levels of data may appear as separate fields on a display screen.

Furthermore, the data options also may be depicted as a visual object, such as a graphic representation of an anatomy, or a part of an anatomy. The user may conveniently make a selection by clicking on the appropriate portion of the object shown. For example, under the anatomy category, the user may select from a general portion of the body, such as an arm. The user may also select a type of system, such as a circulatory system, skeletal, etc. A detailed picture of an arm is displayed and the user may click on a target location, such as the median nerve on the upper limb.

The categories usually include clinical presentation, pathology, anatomy, treatment and outcome, in accordance with the present invention. Patient data may be entered for any number or combination of categories, from one to all five categories. In one embodiment patient data for the treatment and outcomes categories are entered. A category may comprise a single or multiple data entry fields. A category may also be depicted on a single or multiple display screens.

The clinical presentation category 56 refers to clinical findings attributed to the diagnosis being described. Clinical presentation includes the signs and symptoms of the condition or the diagnosis of the patient. For the neurosurgery field, example clinical presentation data options are cranial nerve palsy, branching to oculomotor or optic in the next level, painful or painless in the subsequent level, etc.

The pathology category 54 refers to the etiology of the patient's condition. Pathology data describes the causation factors for deviations from normal structure, physiology, biochemistry, cellular biology and molecular biology. The data options are typically grouped by condition type. Examples of first level data options are "genetic," "acquired" and "environmental" etiology factors. There may be multiple influencing causes for a condition. More specific levels of pathology data options may be stroke, tumor, etc. Further narrowing levels of data options may include descriptive selections that indicate the gross appearance of the causation factor, such as type, size, shape, etc. Examples of branching levels of pathology data options are 1) arterial aneurysm; 2) berry, saccular and fusiform; and 3) large, medium and small. Data options having variable terminology, such as size, have clear definitions. In one embodiment, small is less than 10 mm, medium refers to 10–24 mm and large is greater than 24 mm.

The anatomy category 52 refers to the location of the problem in the body. A top level may indicate a general location for the pathological condition. For example, for vascular diseases represented by the formation of an aneurysm, the anatomy category may be listed as arterial or venous and the vessel sites, such as cardiac vein, cranial artery, etc. Subsequent levels may indicate specific vessels affected, such as internal carotid artery (ICA), anterior communicating artery (ACA), posterior communicating artery (PCA), etc. Even lower levels may further localize the precise site, such P1, P2, P3 and P4, the transverse portion of the arch of the aorta, etc.

The treatment category describes the procedure performed on the patient by the healthcare provider. A data option for "none" is included to indicate no treatment was performed on the patient.

The outcome category describes the results of treatment, as well as complications that resulted. Exemplary outcome data options may be general descriptors, such as discharge destination, e.g. "chronic care center," "rehabilitation center," "other acute care hospital," "home/relative," "died," "don't know" and "other." Some outcome data options may represent the state of the discharged patient, such as "dead," "vegetative," "disabled/assistance required," "disabled/ independent" and "normal." The outcome category may also represent more specific complications resulting from the treatment, such as pneumonia, paralysis, cranial nerve palsy. The outcome and complications codes may also be hierarchically related.

Other categories of interest may be chosen to appear in the data entry screens, depending on the application of the data analysis system. In some embodiments, a healthcare provider category is included to allow for quality assurance analysis of specific providers. Exemplary fields for this provider category are practitioner, institution, department, etc.

The user may choose from a list of a variety of display screens. Any convenient user interface screens may be present containing any relevant data entry fields. For example, the display screen may be diagnosis, images, test results, treatment procedures, such as operations, admissions, clinic visits and current status.

The screens may be organized in a hierarchical tree structure or linear structure. For example, a screen with fields for general data may be on one page having buttons to view subsequent pages having fields for more specific data. The screens may also be arranged in a random structure.

Usually, there is a data entry screen that allows for basic patient data to be entered, such as patient demographics. Exemplary open text fields in the demographics screen are fields for to enter patient name, age, address, birthday, etc. Drop-down list text fields may be, for example, a list of relevant past or present illnesses or ethnicity. To facilitate data entry, as part of a data option term is entered, the database may recognize the term and automatically display the data options that complete that term, or if only one data option exists, the database may filled in the rest of the term from the list. In one embodiment, by entering the patient's date of birth the age of the patient is automatically calculated and entered in the age field.

Figure 2A:
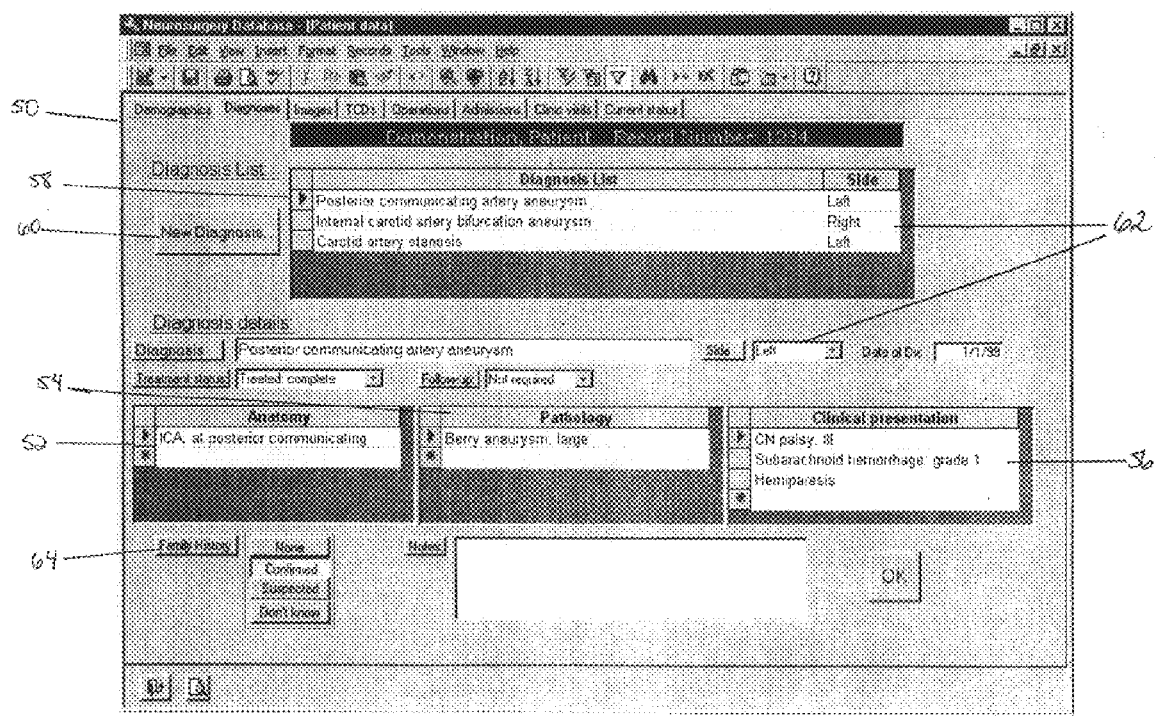
Figure 2B:
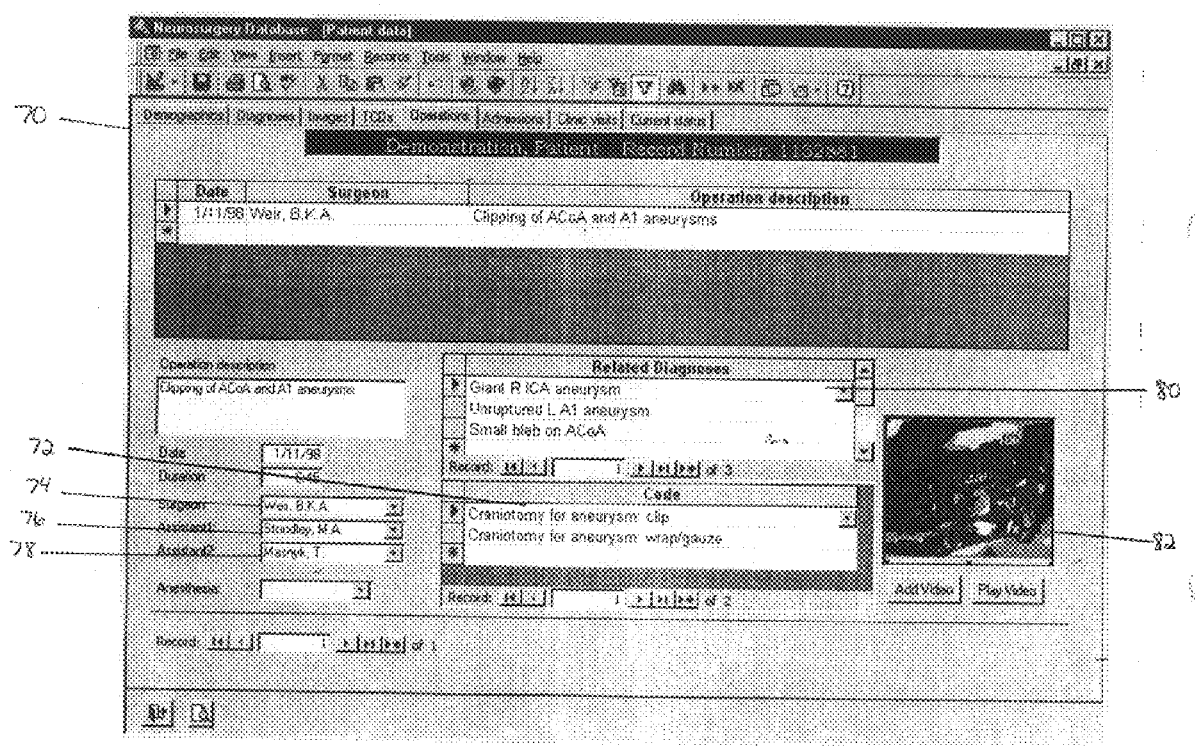
Figure 2C:
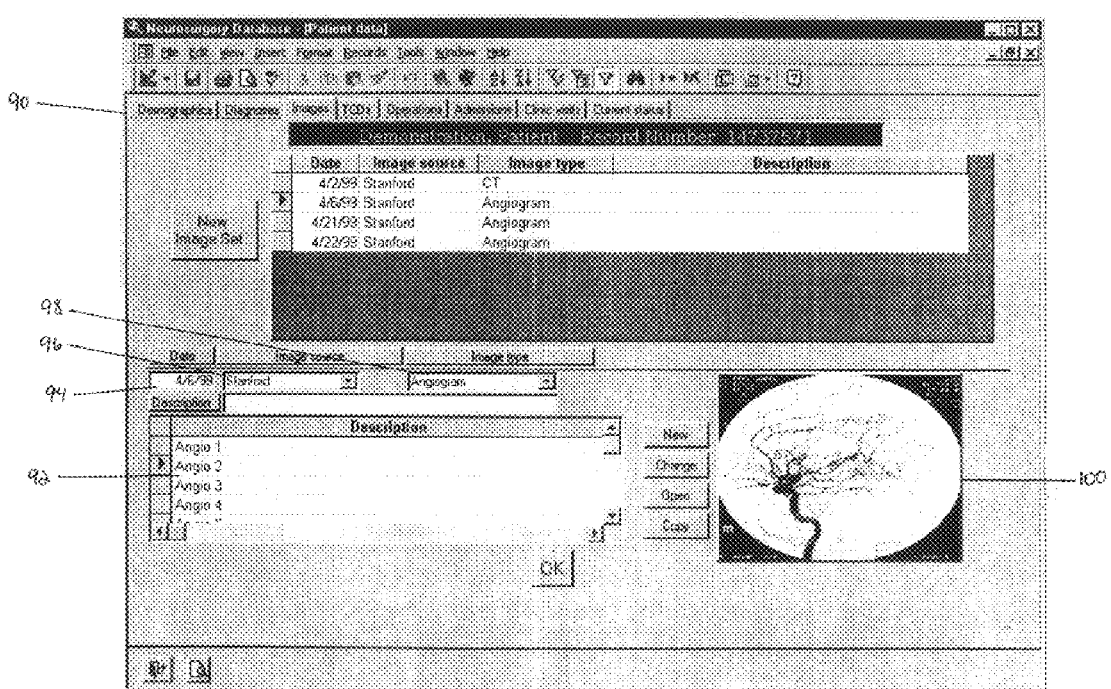
Figure 2D:
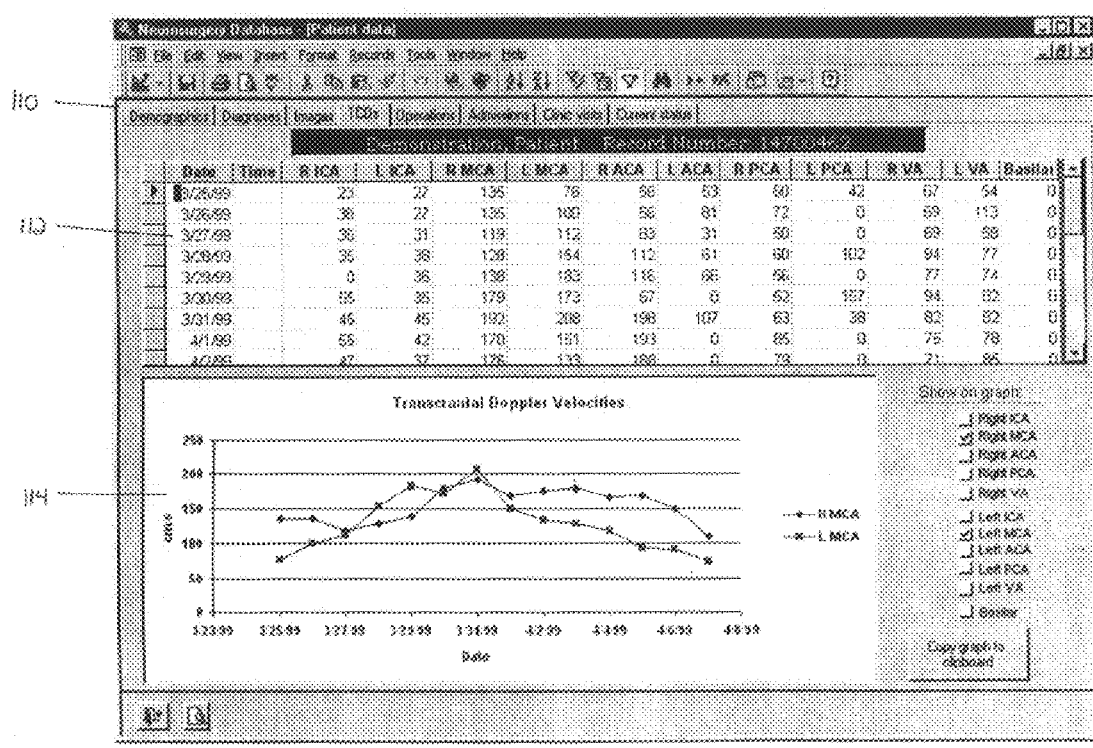

Some typical data entry display screens are shown variously in FIGS. 2A and 2D. FIG. 2A depicts an exemplary diagnosis display screen 50. Categories on the diagnosis screen 50 are shown by fields for anatomy 52, pathology 54 and clinical presentation 56, which allow for any number of data to be entered from a drop-down list of data options. The diagnosis screen 50 has a diagnosis list 58 of stored diagnoses for the current data set and several fields for entering and viewing detailed information related to the diagnoses. A new diagnosis button 60 is provided for entering new diagnosis and diagnosis details. Usually, the diagnosis field is an open-text field. Furthermore, the proximal location relevant to the diagnosed condition is provided for each diagnosis as a separate field, entitled, "side" 62 to further describe the diagnosis. Data options in the side field are "left," "right" and "midline," to indicate the general location of the diagnosed condition. In addition, an indication of family history 64 may be selected as "none," "confirmed," "suspected" or "don't know."

An example treatment screen is the operation screen 70 shown in FIG. 2B where details of patient operations are described. The operation screen is associated in storage within the database tables including an operation table 150 and operation code table 160, both described in detail below. Shown in the operation screen 70 is a field for codes 72 for which any number of data options may be selected as patient data describing an operation. The operation screen 70 also includes data entry fields for the practitioners responsible for the procedures performed by the surgeon 74, assistant 176 and assistant 2 78. In the related diagnosis field 80 the user may select from a list of diagnoses previously entered for the patient in the diagnosis screen 50, described below. Thus, in memory, the operation table 150 also relates to a diagnosis table for the diagnosis screen 50. In this manner, one may record which diagnoses an operation addresses. In addition, a video clip taken during the procedure may be attached to the video window 82 and the relationship of the video to the operation may be stored in the database with the patient data set. The attached video provides an invaluable record of the treatment.

Further to variations on data entry screens, images may be inputted into the image screen 90 shown in FIG. 2C. Text data is entered for each image depicted in the field entitled description 92. Other fields for text data include data 94, for the date the image was produced and image type 98. The field for image source 96 allows the user to label where the image was acquired, such as a department or institution. Individual images in a study may be shown in the image window 100 by selecting the image form the list in the description field 92. An image may be viewed in an enlarge mode such that a new screen appears displaying the expanded image. New images may be imported into the database and into the image screen 90 from the storage unit in the computer platform, remotely located servers that are in communication with the user station, etc.

Another optional display screen shows the test results for a given patient. FIG. 2D illustrates a TCD screen 110 for the results of ultrasound studies on specific vessels in the form of transcranial doppler velocities (TCD). The data from selected vessels are listed in table 112 and represented on graph 114. Graph 114 is a plot of velocities of blood flow rate (cm/sec) within the selected vessels over a course of dates.

An alternative feature of the data analysis system is an opportunity to create custom screens that include specific fields related to any data option in a category. The custom screen allows the user to enter extra useful information associated with a selected data option. A user may custom design and store a screen to appear for future data entry. In order to create a custom screen, the user specifies the data option to which the custom screen relates.

This custom screen feature enables the database to be used for virtually any prospective clinical study, such as a clinical trial or testing of a new medical procedure. Thus, in addition to conducting retrospective analyses on already stored patient data, a practitioner may use the present database to collect and analyze pertinent data on patients included in a defined study group as a clinical study is taking place. This feature is a great advantage over typical medical databases where a new and separate database must be programmed for special investigations. Separate databases used for prospective studies do not conveniently link to patient data in other databases. However, the present invention provides for links between the custom prospective data and the other patient data. The medical database may recognize which data options the custom screen data relates to, how to link a patient data set and when to display the custom screen during data entry.

To illustrate one example of a custom screen, e.g. custom prospective screen a link may exist to the data option in the pathology category, labeled "berry aneurysm." As the data option, "berry aneurysm" is selected by the user, a custom screen entitled, subarachnoid hemorrhage (SAH) appears allowing the user to enter data related to an SAH. In the SAH custom screen, the activity of the patient at the time of the hemorrhage may be described, as well as the specific classification of the hemorrhage and the results of procedures, such as a lumbar puncture.

Figure 3:
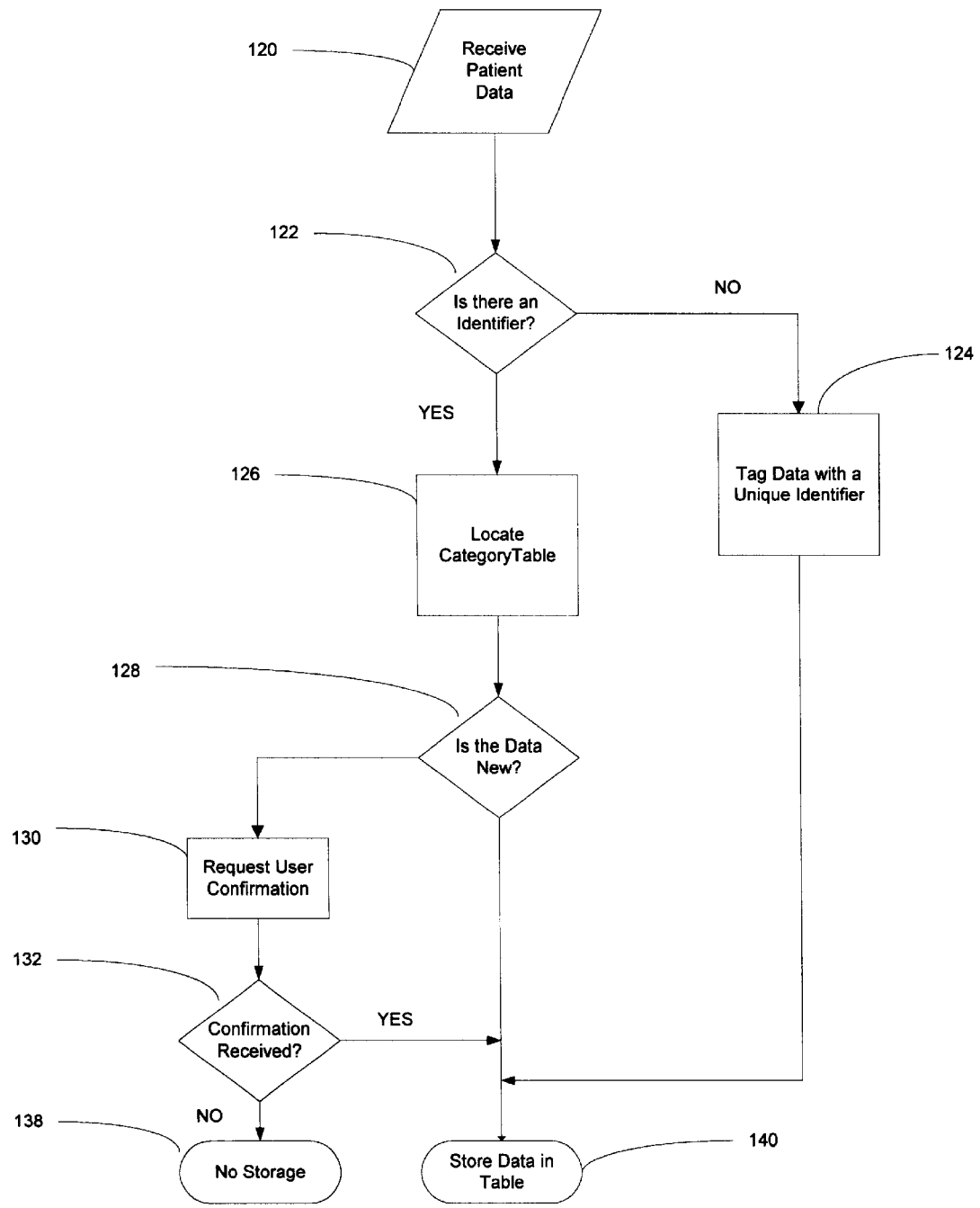
FIG. 3 is a flow diagram of one method of storing medical patient data, in accordance with the teachings presented herein.

As the data are obtained from the input device and enter the platform, the data are examined by the tagging component of the database to determine the whether the incoming data are related to an existing data set or are a new data set. FIG. 3 shows one process used in the storing of entered data by the user station 10 depicted in FIG. 1. The patient data is received 120 by the database 22. The database checks 122 to see if the incoming data has an identifier. If there is no identifier to the data, the tagging component 24 assigns 124 a new identifier to the data and places the data into storage 140. Typically, the identifier is a string of binary numbers. If the data has an identifier, the data is sent to the storage to either replace existing data from the data set or as additional information to stored data. The appropriate data table is examined 126 to determine whether the incoming patient data is already present in storage 128. The incoming data may be a copy of data stored in a data set, such as the same treatment data option, or a duplicate of a typically unique field, such as patient name. Where the data is already a copy of stored data, the user is notified that the data is duplicate and requests confirmation 130 that the new data should be added. If confirmation is received 132, the new data is stored 140. Otherwise, if no confirmation is received, the data is not stored 138.

It should be noted that the steps in FIG. 3 may be performed in various sequences and other steps may occur. In other embodiments, the user instructs the platform that the data is a new data set and an identifier is automatically assigned to the new data set prior to the data entering the storage unit.

In general, a relational database comprises a series of data structures, in the form of tables having columns and rows, containing information linked through common fields. The database uses these structures to store, retrieve and manipulate patient data. The relationships between tables are established within the database to allow particular tables (and their associated screens) to point to other tables within the database. This pointing relationship allows the particular related tables to exchange or to associate their information with each other during a data search.

The medical patient data is organized by the present data analysis database into tables for each category. As shown in FIG. 4A, operation table 150 stores patient data entered on the operation data entry screen 70 for each data set. The columns on the operation table 150 represent fields on the operation screen. Data from single entry fields, e.g. only one datum is permitted to be entered, are shown in single datum columns 152, "Patient ID," "Date," "Operation," "Duration," "Surgeon," "Assistant 1," "Assistant 2" and "Anesthesia." Fields for which multiple data may be entered are shown in a related linked table. To illustrate, the column entitled Operation ID 154 contains data that is related to Operation codes table 160. Thus, all operation codes 164 for patient A having operation ID 1 156, are shown in the operation table also listed as Operation ID 1 162. This link allows almost any amount of data to be entered for a given record.

There may be similar data tables for each screen, such as demographics, diagnosis, operation, clinic visits, and current status. These screen data tables may be linked to category tables for fields that allow for multiple entries per record on the screen. These category data tables include clinical presentation, anatomy, pathology, treatment and outcome. Furthermore, specific entries in the category data tables may also be linked to custom detail tables, e.g. custom prospective tables having custom prospective data.

The data options are arranged in the data option tables according to levels in a hierarchical tree. The data in various levels of the tree maintain their relationship to data in the other levels of the tree. It is recognized that data at lower levels are more narrowly described subsets of data in higher levels of the branch. Data entered from custom screens also may maintain their relationship to the data located at various levels of the tree.

FIG. 5 shows one anatomy data option table 170 for data options in the anatomy category. The columns represent levels 172, which have various data options 174. Level 1 contains the data option, "upper limb." The next lower level, level 2, branches into two options, "elbow" and "hand." Level 3 contains data options "index finger" and "thumb" positioned under the "hand" branch.

All data are associated to their data set across the various tables of categories by the assigned identifier. All data of a data set, including multimedia data are related through the common identifier. Where data, such as multimedia data, are stored in a remote unit, a table is provided to cross-reference the identifier with the identification used by the remote unit. After the data are organized, the database sends the data to the storage unit where it is available for retrieval by the database.

In some embodiments, the data are further manipulated prior to storage by the processor compressing the data. Some data are very large and compression permits conservation of storage space. For example, an MRI study on a patient may include text and about 100 images, each of which may be 300 to 500 Kb in size, loading to a study of 50 to 80 Mb total of data. In the absence of compression, this large amount of data may present a particular problem for the storage of medical information.

Generally, compression formats are either high or low efficiencies. Low compression schemes, i.e. those that do not provide significant compression ratios, include graphic interchange format (GIF), bitmapped image compression schemes and tagged image file format (TIFF) compression schemes. Alternatively, high efficiency compression formats may be employed, such as wavelet, motion wavelet, Motion Picture Experts Group (MPEG) and joint photographic experts group (JPEG) schemes.

Compression formats may also be either lossy or lossless. Lossy compression schemes are characterized by components of an original image being absent from a reconstructed image after a compression-decompression cycle. Lossless schemes do not surrender any information.

Data Searches

The user may search any of the categories in the various display screens. Usually the search is a Boolean format, but advanced search strings may also be employed. The user requests a particular search screen, for example, by selecting a search button in the main menu.

Where data in the categories are being searched, the selected categories may be chosen from the search screen. The specific categories are chosen to provide the most accurate results for the analysis. Usually the search categories include one or more of clinical presentation, anatomy, pathology, treatment and outcome. Often at least two categories, at least three or four or all five categories may be chosen.

For example, a search may be conducted for diseases that have been coded with a combination of "internal carotid artery" (anatomy), "giant berry aneursym" (pathology), "painful oculomotor nerve palsy" and not "subarachnoid hemorrhage" (clinical presentation), and "craniotomy to clip aneurysm" (treatment). Such a search may be further refined to locate only those patients suffering from a particular complication of the treatment, by entering the appropriate code in the complications search field. The system also enables broad searches. For example, searching just for the anatomy code "internal carotid artery" will find all patients with diseases of that artery, regardless of the associated pathology, clinical presentation, or treatment. Data entered in a custom prospective screen that is related to a data option in a category may also be included in a search.

Figure 6A:
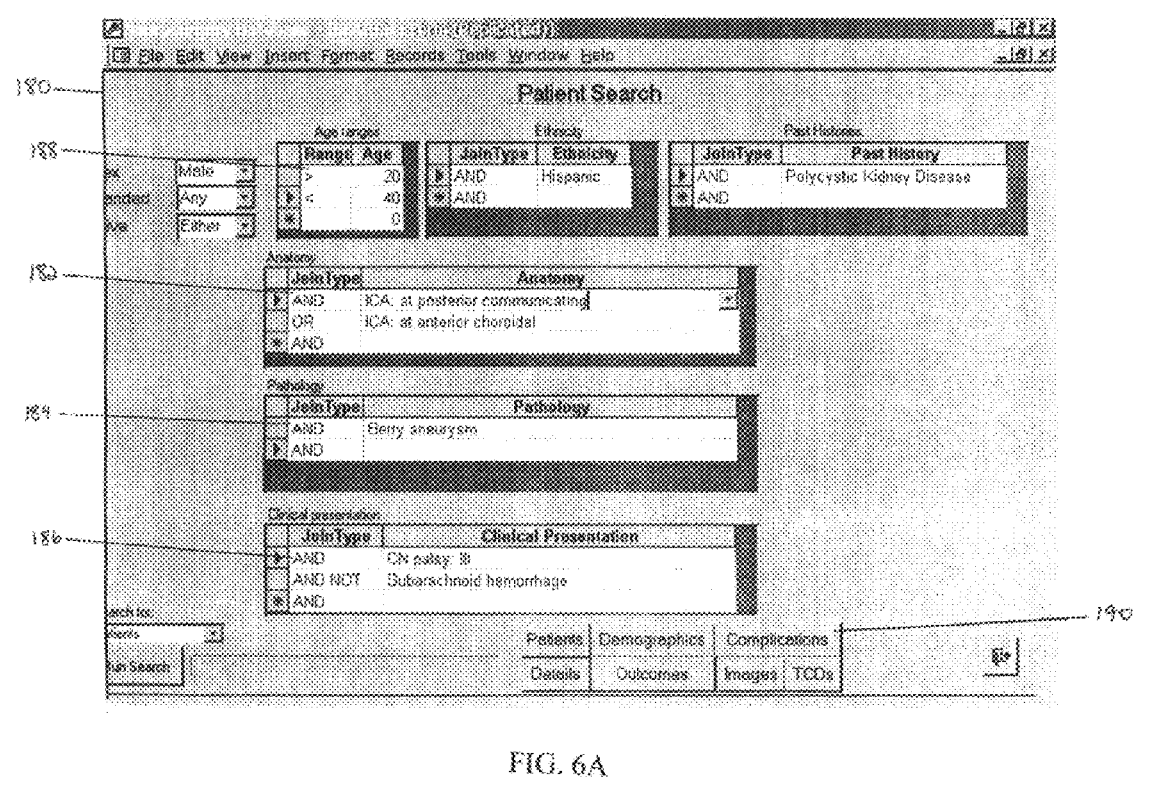
Figure 6B:
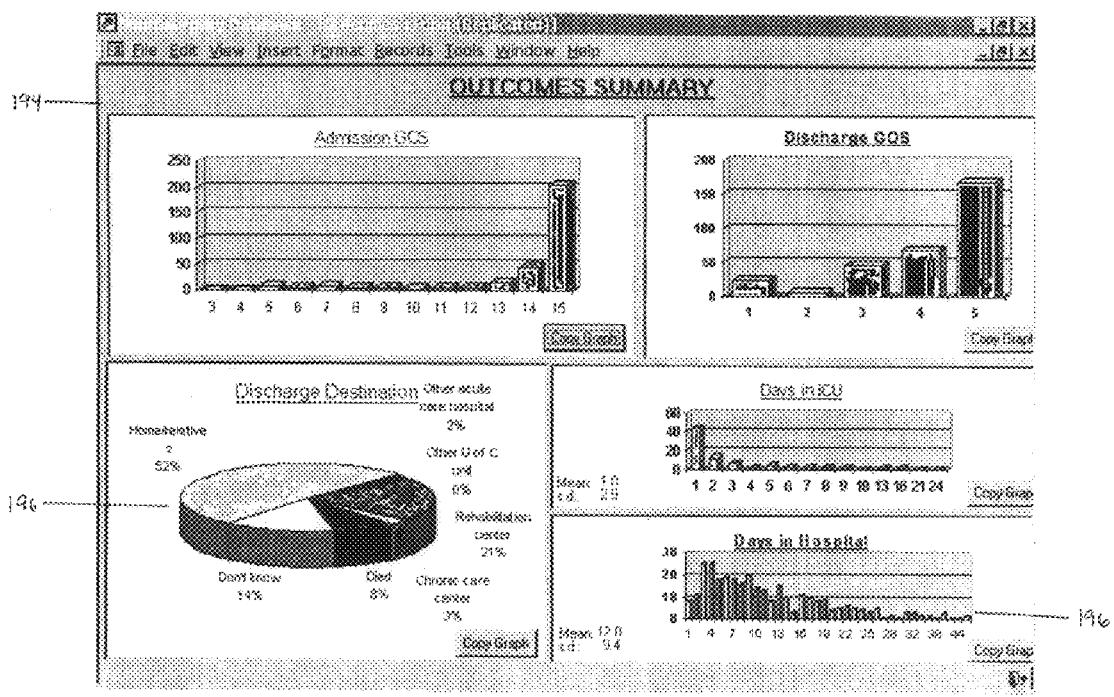

FIG. 6A illustrates one embodiment of patient search screen 180. Search categories include anatomy 182, pathology 184 and clinical presentation 186. The user may insert several search criteria for each category. A patient age criterion is specified in the age field 188 within a range by a less than and greater modifier. It is common for some demographic data to be included in the search criteria. Another useful search method allows the user to extract from a provider category, data on a particular healthcare provider, e.g. individual, department, institution, etc., or group of providers. The user may compare groups of providers with outcome results to assess quality of care rendered by a given healthcare provider. Another application of a provider search is to determine which group of individuals performs particular tasks more often. For example, in a teaching institution, the number of attending practitioners, fellows and residents performing particular operations may be determined.

An advantage of the present data analysis system is that data may be cross-tabulated at any level. The user may request the data from one level and also request more specific data in from lower levels. In this manner, totals of subgroups may be compared as percentages to the overall totals of the larger group and statistical comparisons, such as Chi square tests and Student's t-test may be used on the tabulated data.

Moreover, data searched for retain their relationship to other levels of the hierarchical tree to which the data belongs. Where data relating to a top level are searched for, data associated with that top level are retrieved as well as data from lower levels of its branch. Thus, referring again to the anatomy data option table 170 in FIG. 5, where a search is conducted for all data associated with the hand, data that matches "hand" in level two are retrieved. In addition, the data analysis system retrieves all data entered for lower levels falling under the "hand" row, such as "thumb" and "index finger."

Another feature is that data may be searched in various categories and across different conditions. For example, a search of all patients having conditions localized in a particular part of the anatomy may be easily collected. By comparison, databases using other coding systems, such as ICD codes, have limited searching capabilities on specific patient descriptive information.

The ICD-10 coding system does not have separate categories for descriptive information, such as clinical presentation, anatomy, pathology, treatment and outcome. Rather, ICD-10 lists all information, such as pathology combined with some anatomy information under disease states. Thus, it is difficult or impossible to search for all patients having any disease related to a specific part of the anatomy. As an example, the ICD system may code aneurysms of the ICA as one number and stenosis of the ICA as a different and non-related number. Thus, to search for all ICA related conditions, each disease must be searched in separate steps, whereas with the present invention a search for ICA retrieves all matching data in any selected categories and for any patient conditions.

A further unique benefit of the present data analysis system is that multimedia data may be retrieved based on the patient descriptive information provided with each category. The database may retrieve all multimedia data related to a data set that matches the requested criteria by corresponding identifier. In previous medical analysis systems, images are stored according to a patient identifier alone. Thus, before the present invention, one was required to first create a list of patients and then retrieve the patients' multimedia files individually. There was no way to automatically retrieve in one step, the multimedia data that match a detailed description of the patient's characteristics, e.g anatomy, pathology, outcome, etc.

The type of requested output of information from the search results is selected by choosing from a series of "search for" options 190, such as "patients," "demographics," ""complications," "details," "outcomes," "images," and "TCDs."

When the user station receives a search request from a user, the database searches each table for data matching the criteria. The identifier for the matched data is recognized and the "search for" data with the same identifier is retrieved.

The database performs the requested computations, such as itemizing total numbers of matching "search for" data. The output may be posted as graphic representations, such as pie charts, bar charts, graphs, etc. of the results or in the form of lists or spreadsheet tables. A summary of outcome data from an example search is shown in the screen 194 FIG. 6B having graphic representations 196 of search results.

Presentations

Oftentimes, the results of an analysis study are to be presented to others in the form of a report, slide, transparency, handout, etc. For convenience, the present analysis system permits a user to download the results of a search query to a graphics software application, e.g. Power Point® by Microsoft Corporation.

Figure 7:
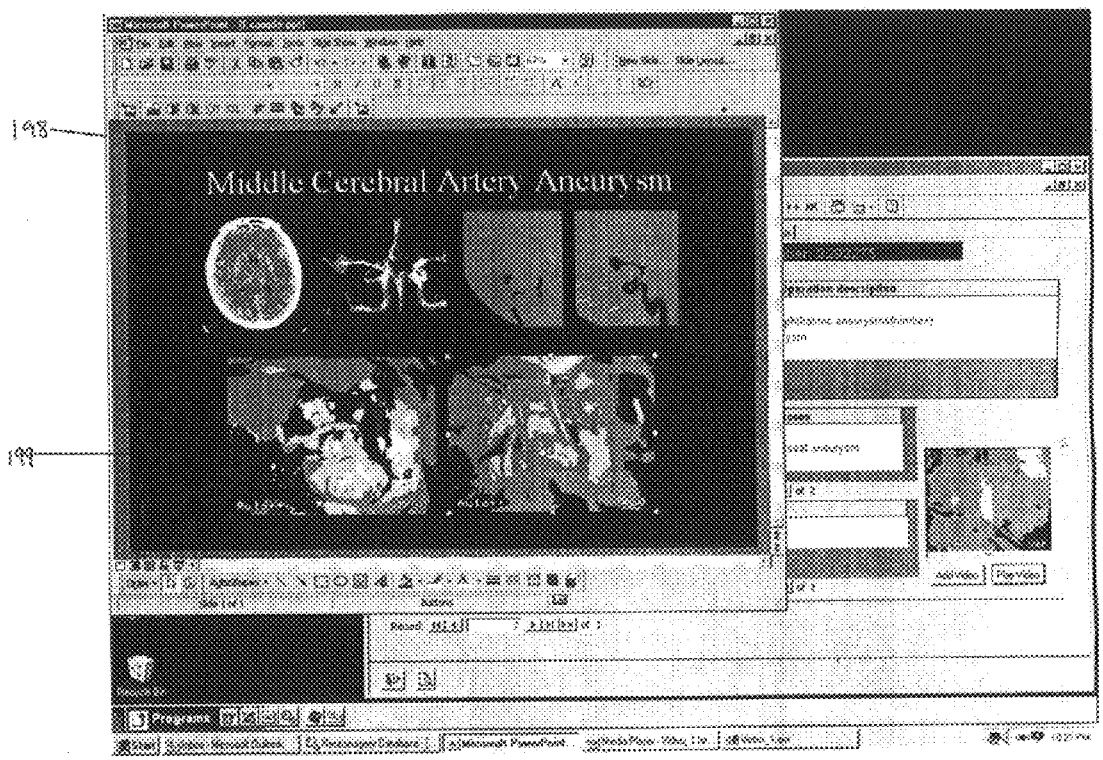
FIG. 7 is an example of a presentation screen for presenting particular patient data resulting from a search of patient data stored in one relational database, in accordance with the methods described below.

As shown in FIG. 7, various images may be selected and downloaded onto a presentation slide 198. Furthermore, the user may freeze a frame in a video and transfer the frame 199 to the presentation slide, or use the entire video, or portions thereof, in a computer presentation. The images may be manipulated prior to transfer by zooming, cropping, enlarging, reducing and the like.

Network System

In other embodiments of medical patient data analysis system, in order to avoid overloading a computer station, a client-server architecture is used, for example, where data storage, processing and control of data are implemented on a server that is in communication with the user station. Thus, a server may include a storage device and processor. Optionally, computations with the data may be performed on the server as well. In this client-server embodiment, the server is communicatively coupled to one or multiple user stations by an Ethernet connection, local area network (LAN), wide area network (WAN), the Internet, etc.

Figure 8:
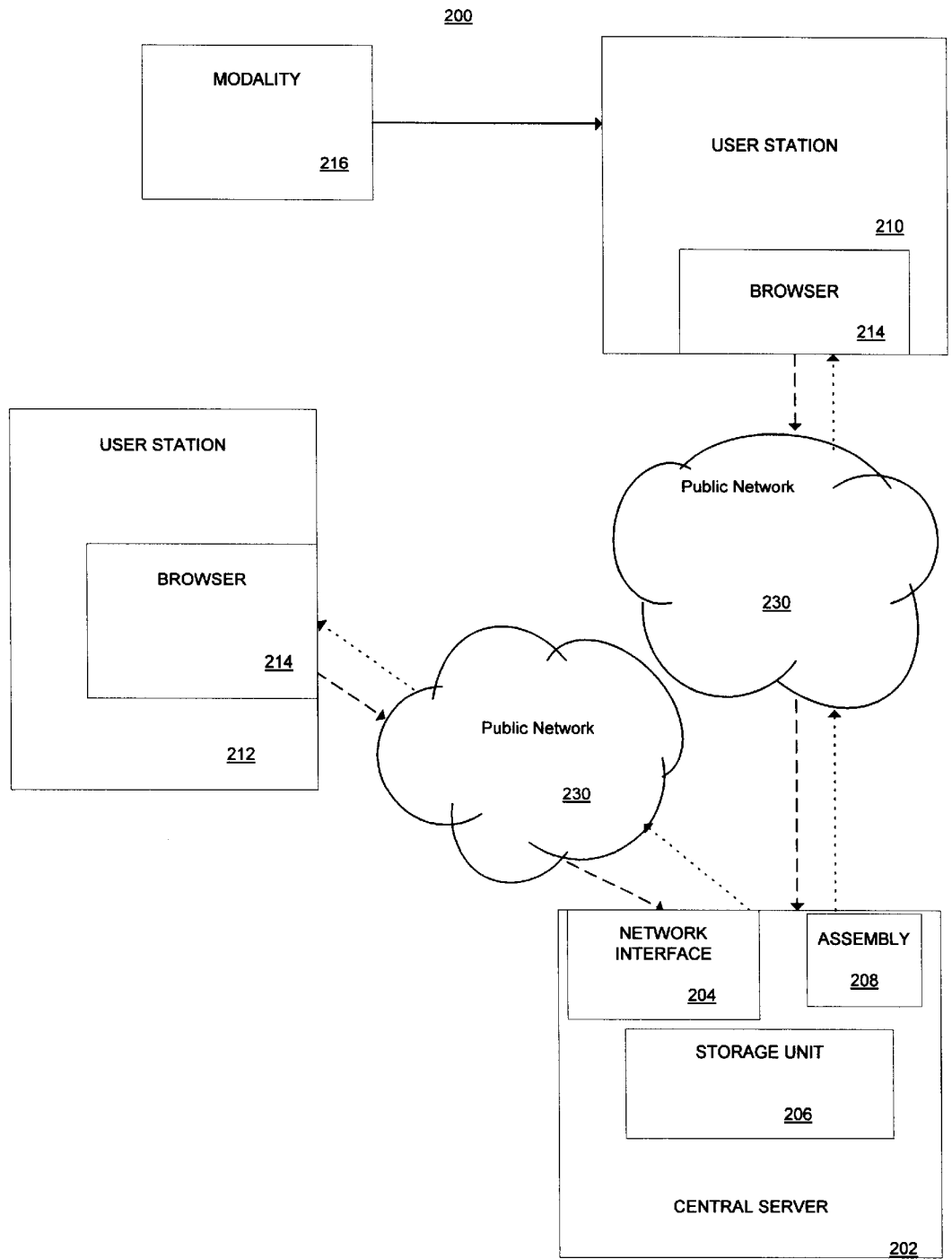
FIG. 8 is a block diagram of one embodiment of a medical data analysis network system configured, in accordance with the teachings presented herein.

In one exemplary patient data analysis method, a server stores multimedia data for access by a remote or local user station. In another embodiment, of a patient data analysis system 200 shown in FIG. 8, a central server 202 accumulates and stores all medical patient data that is sent by user stations 210 and 212. User station 210 receives raw data from modality 216 and transfers the data to the server 202. The server 202 includes a network interface 204 for acquiring the medical patient data from each of the user stations and sending the selected portions of medical patient data into the network for receipt at the requesting user station. The server further has a storage unit 206 coupled to receive and to store the medical patient data from the network interface. An assembly unit 208 in the server is coupled to the network interface 204 and storage unit 206 to gather selected portions of the medical patient data in response to instructions from a user station. The user station is coupled to the server by a public network across the Internet.

The user stations 210, 212 may communicate to the central server 202 with use of a browser 214, i.e. Web browser software. The browser 214 issues a request, such as an HTTP request, for a particular user interface, e.g. a Web page. The browser 214 is also used in viewing the user interface. Commercially available browsers include Netscape Navigator® from Netscape Corporation located in Mountain View Calif.; Internet Explorer® from Microsoft Corporation located in Redmond Wash.; and Lotus Notes® from Lotus Development Corporation located in Cambridge, Mass.

A user may request selected data through a search query, as described above for a client-based system. However, in one method of conducting a search, the user must first transfer their patient data to the central server prior to conducting such a request. An activation unit in the server may be present to determine whether patient data were received from a user station prior to the user sending instructions for selected portions of patient data. Thus, upon requesting a search, the user is prompted to transmit patient data from the user station to the server.

One method of exchanging medical patient data across a network involves the user station assembling data into packets. The user station sends the packets into the network for receipt at the server. The user selects criteria from at least one of the patient descriptive categories, including clinical presentation, pathology, anatomy, treatment and outcome. The user then requests the selected patient data associated with the criteria from the server. The server receives the request and retrieves the appropriate patient data in a manner similar to the method used by the user station described above. The user station receives the selected medical patient data from the server.

In this manner, any number of user stations may be members of a medical network enterprise and access a central collection of patient data stored in a server. A given user station may have access to enormous amounts of patient data from healthcare sources anywhere in the world. In one application, data from multiple practitioners are accumulated for defined clinical trial studies. In other applications, audits and quality assurance activities may be conducted on specific medical disciplines.

In order to protect the confidential nature of the patient information, usually the patient data set is stripped of data that may identify the individual patient. For example, the patient's name, address, social security number, etc. is protected. There are several ways of securing this personal data. In one embodiment, the personal data is not forwarded to the central server. Alternatively, the central server may receive the personal data and remove this data from the data set prior to storing the data. In other cases, the central server may store the personal data but restrict access to the sensitive data, such as by removing the personal data from the selected data prior to sending the data to a user station.

The present medical patient data analysis system and method for its use, may facilitate any clinical studies and quality assurance. The invention is particularly beneficial in the neurovascular surgery field, where the present database may produce an audit that includes aneurysm characteristics, admission grade, lengths of intensive care, hospital stay and outcome score. Outcome can be correlated with factors such as vasospasm, intraoperative blood pressure, ventricular drainage, intraoperative angiography and temporary clipping. The invention may be used to track patients with untreated problems, such as incidental aneurysms. The recorded images and video clips may be applicable in teaching or producing presentations and reports.

To further protect the transferred data, the user station may encrypt the data prior to data transmission. A variety of encryption schemes may be used, such as public key encryption or private key encryption. The encryption components may be stand-alone components or software components executed by the processor in the user station. The central server includes a decryption unit for decrypting the received data prior to storage.

To make transmission more efficient, the data may be compressed prior to sending. The compression schemes employed may be similar to the compression formats used prior to storage as described above.

The present invention has been described above in varied detail by reference to particular embodiments and figures. However, these specifics should not be construed as limitations on the scope of the invention, but merely as illustrations of some of the presently preferred embodiments. It is to be further understood that other modifications or substitutions may be made to the described information transfer system as well as methods of its use without departing from the broad scope of the invention. Therefore, the following claims and their legal equivalents should determine the scope of the invention.

What is claimed is:

1. A computer assisted method for analyzing medical patient data comprising:
   instructing a relational database to access stored patient data of data sets, each data set being for a different patient and having a unique identifier, the patient data being located in tables of categories including clinical presentation, pathology, anatomy, treatment, and outcome, and the patient data of a data set related to each other by the identifier;
   entering at least one criterion for at least one category; and
   retrieving patient data for all data sets in a group matching the criterion and multimedia data related to the patient data by the identifier.

2. The method of claim 1, wherein the stored patient data is one level of a category hierarchical tree having data options arranged in decreasing levels of specificity.

3. The method of claim 2, wherein the data sets of the retrieved patient data matches criterion from the selected criterion and criterion from lower levels of the hierarchical tree.

4. The method of claim 1, further including the steps of selecting data from the multimedia data and transferring the selected multimedia data to a presentation applications file.

5. The method of claim 1, wherein the particular patient data is associated with criteria from at least two of the categories.

6. The method of claim 5, wherein the particular patient data is associated with criteria from the treatment category and outcome category.

7. The method of claim 1, wherein the entered criterion is for the outcome category.

8. The method of claim 7, wherein the entered criterion is for complication resulting from treatment.

9. A computer assisted method for analyzing medical patient data comprising:
   selecting patient data from data options in at least two categories including clinical presentation, pathology, anatomy, treatment and outcome, the data options of each category being arranged within tables in a relational database by decreasing levels of specificity in a hierarchical tree;
   storing the patient data with a unique identifier to relate the patient data within a data set, each data set being for a different patient;
   entering at least one criterion for at least one category; and
   retrieving the patient data for all data sets in a group matching the criterion.

10. The method of claim 9, further comprising the steps of calculating the total number of particular patient data and displaying the total number.

11. The method of claim 9, wherein the categories further include a provider category and at least one of the criteria is for particular data from the provider category.

12. The method of claim 9, wherein the particular patient data is associated with criteria from at least two of the categories.

13. The method of claim 12, wherein the particular patient data are associated with criteria from at least the treatment and outcome categories.

14. The method of claim 9, wherein at least one of the data options in at least one of the categories is related to custom perspective data in a custom screen table.

15. The method of claim 9, further including the step of retrieving multimedia data related to the particular patient data by the identifier.

16. The method of claim 9, wherein the selecting of patient data is by pointing to a location on a graphic representation of an anatomy.

17. The method of claim 9, wherein the data sets of the retrieved patient data matches criterion from the selected criterion and criterion from lower levels of the hierarchical tree.

18. A medical information system for patient data analysis comprising:
   A) a processor
   B) an input device in communication with the processor for receiving patient data;
   C) a storage unit in communication with the processor having a relational database for:
      (i) storing data within option category tables by decreasing levels of specificity in a hierarchical tree, the data option category tables selected from the group consisting of clinical presentation, pathology, anatomy, treatment and outcome, and
      (ii) storing patient data of data sets, each data set being for a different patient and having a unique identifier within category tables, the patient data being chosen from the data options in at least one option category table,
   the processor comprising:
      (i) a means for receiving patient data from the input and storing the patient data in the storage unit;
      (ii) a means for receiving instructions from the input entering at least one criterion for patient data from at least one category table; and
      (iii) a means for retrieving the entered patient data for all data sets in a group matching the criterion.

19. The system of claim 18, wherein the medical data includes multimedia data.

20. The system of claim 18, further comprising a display in communication with the processor.

21. The system of claim 18, wherein at least one data option is related to custom prospective data in a custom screen table.

22. A computer readable medium having stored therein a plurality of sequences of instructions, which, when executed by a processor, cause the processor to:
   receive medical patient data of a data set from an input device, the patient data being a selected data option from a hierarchical tree having data options arranged in decreasing levels of specificity and each data set being for a different patient;
   determine whether the patient data includes an identifier and if no identifier is present, attach a unique identifier to the patient data;
   store the patient data in a relational database within tables of categories selected from the group consisting of clinical presentation, pathology, anatomy, treatment and outcome; and
   responsive to instructions received from the input device, retrieve particular patient data for all data sets in a group matching entered criterion.

23. The computer readable medium of claim 22, further including additional sequences of instructions, which, when executed by the processor, cause the processor to calculate the total number of particular patient data and displaying the total number.

24. The computer readable medium of claim 22, wherein the particular patient data are from at least two of the categories.

25. The computer readable medium of claim 22, wherein the patient data is stored in a custom screen table related to at least one of the data options.

26. The computer readable medium of claim 22, wherein the particular patient data includes multimedia data.

27. Computer readable instructions, which when executed cause a processor to:
receive medical patient data of a data set from an input device, the patient data being a selected data option from a hierarchical tree having data options arranged in decreasing levels of specificity and each data set being for a different patient;
determine whether the patient data includes an identifier and if no identifier is present, attach a unique identifier to the patient data;
store the patient data in a relational database within tables of categories selected from the group consisting of clinical presentation, pathology, anatomy, treatment and outcome; and
responsive to instructions received from the input device, retrieved particular patient data for all data sets in a group matching entered criterion.

28. The computer readable instructions of claim 27, further including additional sequences of instructions, which, when executed by the processor, cause the processor to calculate the total number of particular patient data and displaying the total number.

29. The computer readable instructions of claim 27, wherein the particular patient data are from at least two of the categories.

30. The computer readable instructions of claim 27, wherein the particular patient data includes multimedia data.

31. A medical patient data analysis server comprising:
A) a network interface for acquiring patient data of a data set from a network, each data set being for a different patient, and sending selected portions of the patient data into the network, the patient data being at least one chosen data option from a hierarchical category tree having data options arranged in decreasing levels of specificity;
B) a storage unit coupled to receive the patient data from the data interface and to store the patient data within tables of categories selected from the group consisting of clinical presentation, pathology, anatomy, treatment, and outcome and the patient data of a data set having a unique identifier;
C) an assembly unit coupled to the network interface and storage unit to gather selected portions of the patient data in response to instructions from a user station for all data sets in a group matching entered criterion.

32. The server of claim 31, further comprising an activated unit for determining whether patient data was received by the user station sending instructions for selected portions of patient data.

33. The server of claim 31, wherein the patient data includes multimedia data.

34. A medical patient data analysis user station comprising:
A) an input device for receiving patient data;
B) a processor comprising:
i) means for receiving patient data from the input device, the patient data being a chosen data option from a category having a hierarchical tree of data options arranged in decreasing levels of specificity, the category selected from the group including clinical presentation, pathology, anatomy, treatment and outcome, and
ii) means for forming instructions by selecting at least one criterion from at least one of the categories; and
C) a browser for sending the instructions and the patient data into a network and receiving selected portions of patient data from the network.

35. The user station of claim 34, wherein the patient data includes multimedia data.

36. The user station of claim 34, further includes a computer readable medium configured to store the patient data.

37. The user station of claim 34, wherein the particular patient data is associated with criteria from at least two of the categories.

38. A method of exchanging medical patient data for analysis comprising:
assembling into packets patient data of data sets, each data set being for a different patient, the patient data being a chosen data option from a category having a hierarchical tree of data options arranged in decreasing levels of specificity, the category selected from the group including clinical presentation, pathology, anatomy, treatment and outcome;
entering at least one criterion from at least one of the categories;
requesting selected medical patient data associated with the at least one criterion from a server;
sending the packets into a public network for receipt at the server; and
receiving the selected medical data for all data sets in a group matching entered criterion from the server.

39. The method of claim 38, wherein the patient data includes multimedia data.

40. The method of claim 38, further including the step of encrypting the patient data prior to sending the packets.

* * * * *

UNITED STATES PATENT AND TRADEMARK OFFICE
CERTIFICATE OF CORRECTION

PATENT NO. : 6,611,846 B1
DATED : August 26, 2003
INVENTOR(S) : Marcus A. Stoodley It is certified that error appears in the above-identified patent and that said Letters Patent is hereby corrected as shown below:

Column 1,
Lines 58-59, replace "Is there supposed to be a journal name here? 1995;60:1541-21." with -- Quality Initiatives and the Power of the Database: What They Are and How They Run," *Ann Thorac Surg*, 1995, 60:1514-21. --.

Signed and Sealed this

Eighteenth Day of May, 2004

JON W. DUDAS
*Acting Director of the United States Patent and Trademark Office*